United States Patent [19]

Dorman

[11] 4,299,220
[45] Nov. 10, 1981

[54] IMPLANTABLE DRUG INFUSION REGULATOR

[75] Inventor: Frank D. Dorman, Minneapolis, Minn.

[73] Assignee: The Regents of the University of Minnesota, Minneapolis, Minn.

[21] Appl. No.: 35,535

[22] Filed: May 3, 1979

[51] Int. Cl.³ .............................................. A61M 7/00
[52] U.S. Cl. ................................................... 128/260
[58] Field of Search ........ 128/204, 29, 205.15–205.16, 128/207.16, 213 R, 214 F, 260, 274, DIG. 12–DIG. 13; 137/487, 489, 500; 417/299, 302–303

[56] References Cited

U.S. PATENT DOCUMENTS

| 2,219,408 | 10/1940 | Benz et al. ........................ 137/153 |
| 3,028,876 | 4/1962 | Gratzmuller ....................... 137/501 |
| 3,731,681 | 5/1973 | Blackshear et al. ................ 128/260 |
| 4,043,332 | 8/1977 | Metcalf ........................... 128/214 E |
| 4,056,095 | 11/1977 | Rey et al. ......................... 128/260 |
| 4,084,612 | 4/1978 | Baehr ............................. 137/484.2 |
| 4,106,510 | 8/1978 | Hakim et al. ...................... 128/274 |
| 4,193,397 | 3/1980 | Tucker et al. ..................... 128/214 F |
| 4,209,014 | 6/1980 | Sefton ............................. 128/260 |

Primary Examiner—C. Fred Rosenbaum
Attorney, Agent, or Firm—Burd, Bartz & Gutenkauf

[57] ABSTRACT

An implantable flow regulator for the infusion of drugs into an animal body from a pressure actuated drug delivery device, such as an implantable infusion pump. The flow regulator comprises a body having a shallow cavity divided into two chambers by a flexible diaphragm. The first of these chambers is a pressure sensing chamber. The other is a valving chamber through which the drug flows, the outlet from that chamber being centrally disposed underlying the diaphragm whereby flexing of the diaphragm in one direction as a result of increased pressure in the other chamber contacts an elastomeric sealing ring around the outlet and closes off the flow path. At least one capillary restrictor is disposed in the flow line between the drug delivery device and flow regulator. The pressure drop across this restrictor governs operation of the flow regulator valve.

17 Claims, 5 Drawing Figures

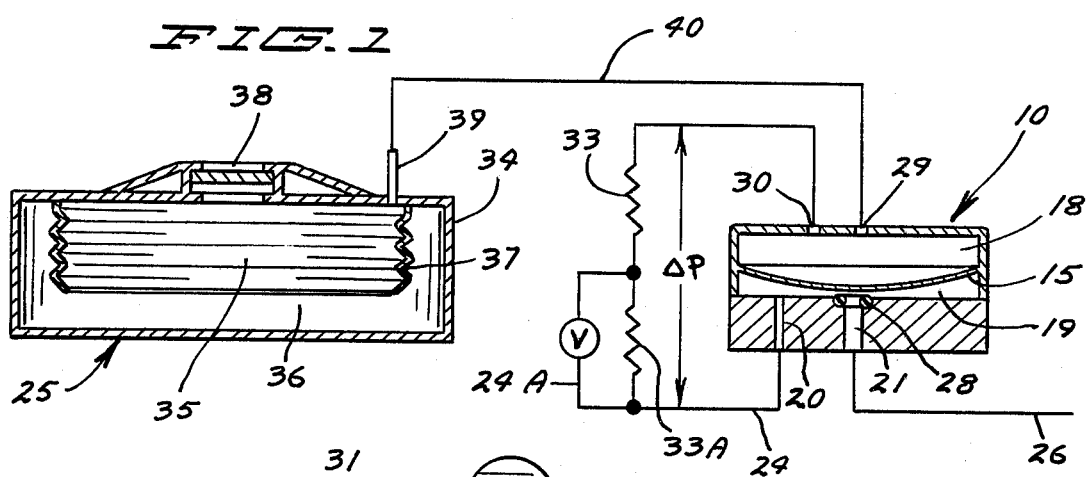
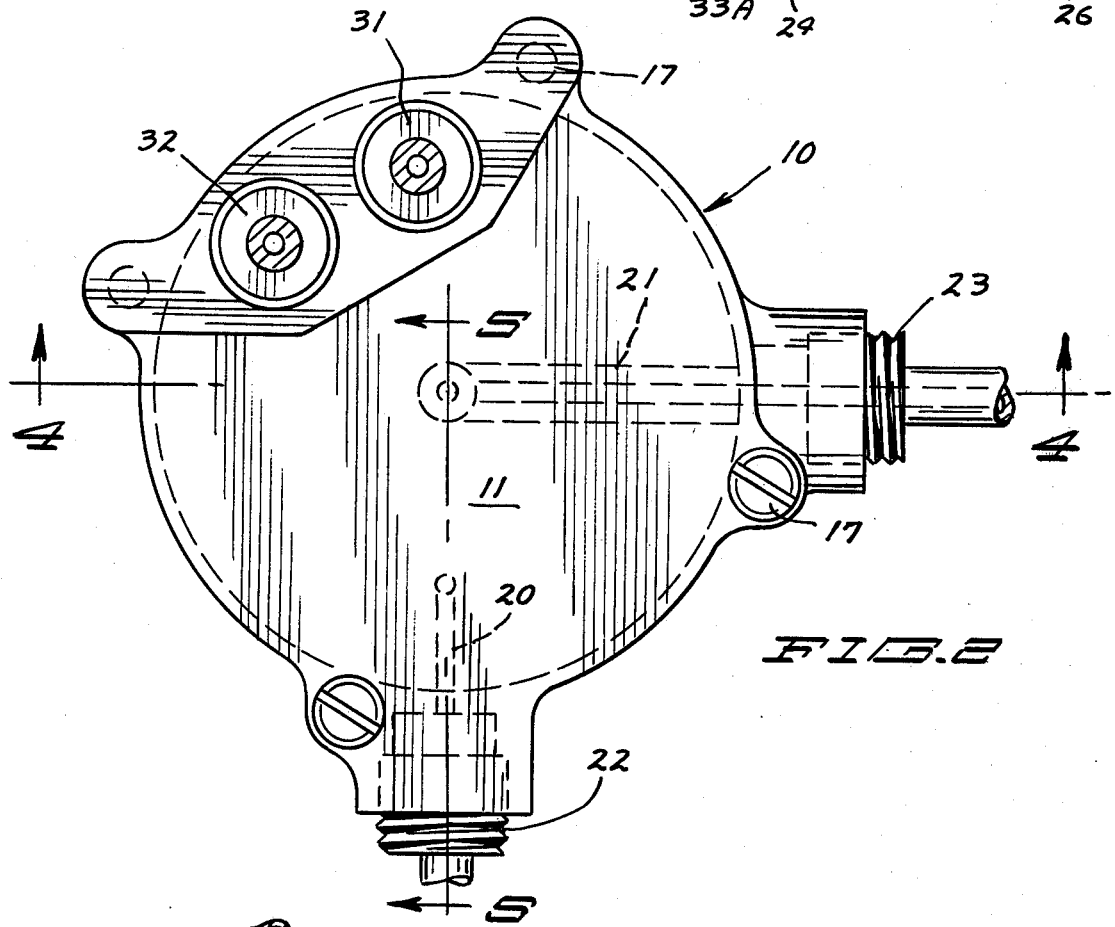
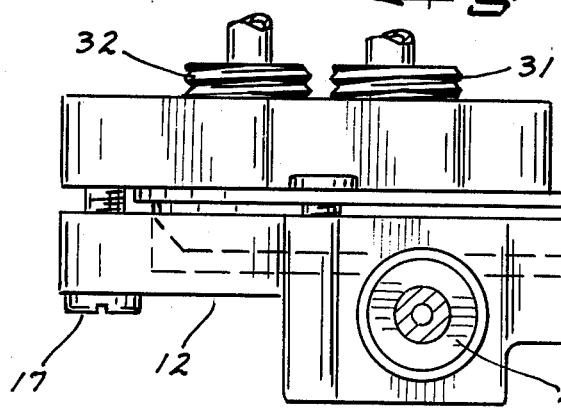

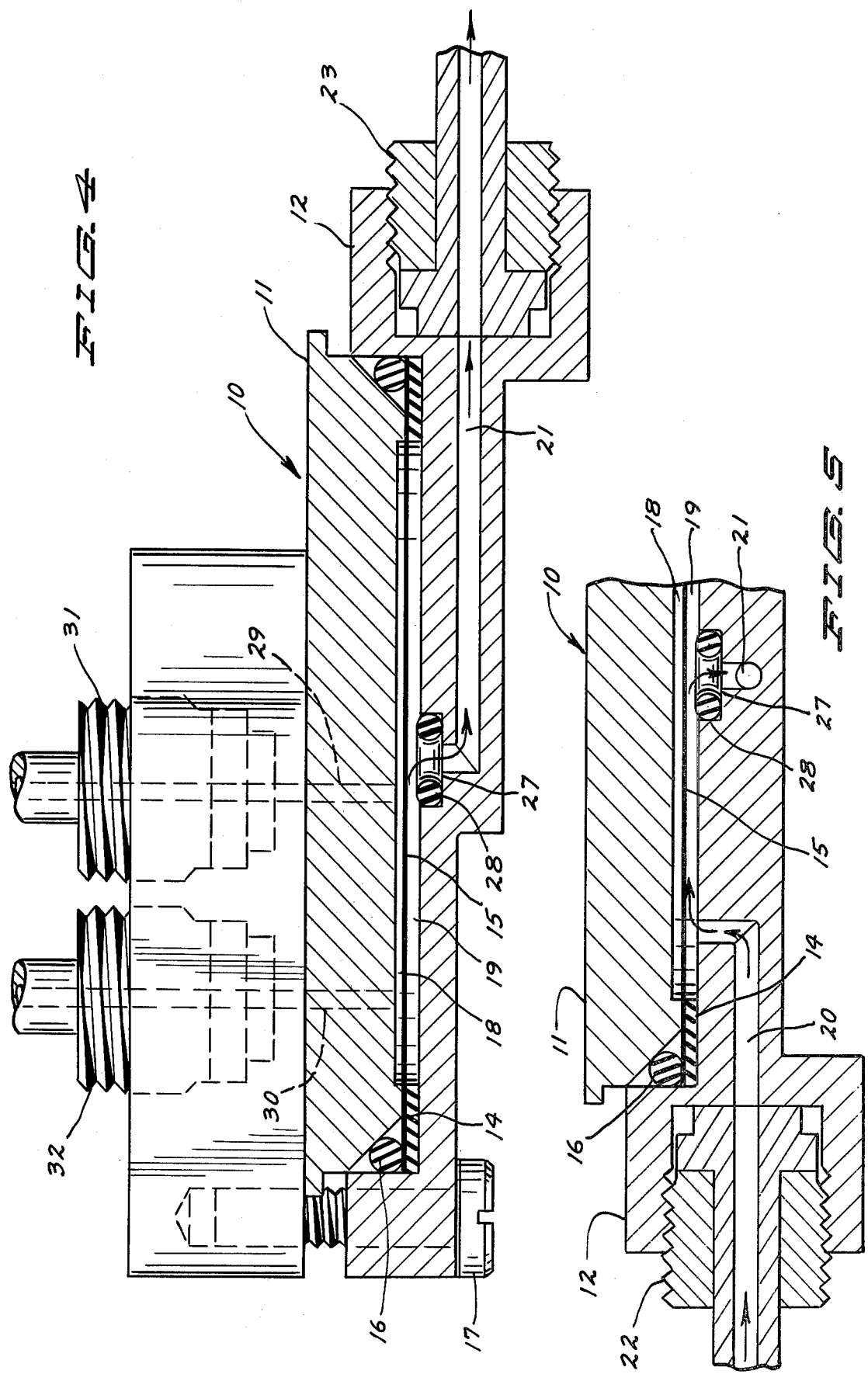

IMPLANTABLE DRUG INFUSION REGULATOR

The invention described herein was made in the course of work under a grant or award from the Department of Health, Education and Welfare.

BACKGROUND OF THE INVENTION

1. Field of the Invention

This invention is directed to an accessory device for accurately controlling the flow rate of drugs from drug delivery devices, implanted or external, that depend on a fluid restriction to limit the flow rate from a pressurized drug storage chamber. One device of this type is the implantable infusion pump illustrated and described in U.S. Pat. No. 3,731,681, the disclosure of which is incorporated herein by reference.

2. The Prior Art

U.S. Pat. No. 3,731,681 illustrates and describes an implantable infusion pump, or so-called "artificial gland", which uses a liquid/vapor equilibrium to maintain a constant pressure on a drug, such as insulin, flowing through a capillary tube in order to maintain a constant flow rate. This technique of flow control is sensitive to temperature and atmospheric pressure. Because the temperature of the human or animal body remains relatively constant, the vapor pressure also stays constant. Where the patient remains in a local region, the air pressure is a minor variable. However, there are conditions under which both temperature and pressure can change a significant amount. If the patient has a fever, or works in a cold environment, the temperature of the implanted gland can change several degrees. The internal pressure change is about 0.5 psi per degree F. A 25 percent increase in pressure and drug flow rate can result from a fever of 102.5° F. This change is more than can be tolerated when a critical drug is being administered.

A more serious situation results from the reduced air pressure in airplane cabins when the patient is traveling. The standard airplane pressure is maintained at a level corresponding to an altitude of about 5,000 feet above sea level. With a gland using an 8.2 psi internal pressure, this would increase the differential pressure by 26 percent over the sea level setting. Although the drug dosage can be adjusted by changing the concentration of drug in the gland, this is a serious inconvenience and hardship for patients who must travel by air frequently.

SUMMARY OF THE INVENTION

The present invention is directed to a regulator device to compensate for variations in pressure and temperature to insure accurate uniform rate of drug flow. Broadly stated, the implantable flow regulator comprises a body having a shallow internal cavity and a flexible diaphragm in the body dividing the cavity into two chambers. An inlet is provided to each of the chambers. An outlet is provided from the second of the chambers, this outlet being centrally disposed in the wall of the cavity underlying the diaphragm so that flexing of the diaphragm in one direction contacts an elastomeric sealing ring around the outlet and thus closes off the fluid passageway. The inlets of the regulator body are adapted to be connected to a capillary flow line from a pressure actuated drug delivery device. The flow line includes at least one capillary restrictor upstream from the inlet to the second chamber. The outlet from the second chamber of the regulator body is adapted to be connected to a catheter flow line extending to the desired infusion site within an animal body.

The capillary restrictor is thus in series with the flow control valve formed by the outlet and diaphragm. The normal pressure drop across the capillary is less than the minimum pressure drop across both, i.e., the pressure difference between the drug chamber of the delivery device and the outside environment of the infusion site. The pressure drop across the capillary tube is sensed by the diaphragm. When the opposing forces on the diaphragm balance out, the diaphragm is stationary. If the forces are unbalanced, the diaphragm is deflected either to close the valve when the pressure drop is high, or to open the valve when the pressure drop is low.

BRIEF DESCRIPTION OF THE DRAWINGS:

The invention is illustrated in the accompanying drawings in which corresponding parts are identified by the same numerals and in which:

FIG. 1 is a schematic representation of the flow regulator according to the present invention, used in conjunction with an exemplary pressure actuated drug delivery device;

FIG. 2 is a top plan view of the flow regulator;

FIG. 3 is an elevation thereof;

FIG. 4 is a section on the light 4—4 of FIG. 2 and in the direction of the arrows; and FIG. 5 is a fragmentary section on the line 5—5 of FIG. 2 and in the direction of the arrows.

DETAILED DESCRIPTION OF THE PREFERRED EMBODIMENT:

Referring now to the drawings, the flow regulator according to the present invention comprises a body, indicated generally at 10, and made up of mating top member 11 and bottom member 12. The top portion of bottom body member 12 has a deep recess into which the bottom portion of top body member 11 is received in mating relation. A resilient gasket 14 is seated in the bottom of the cavity. A resilient diaphragm 15, composed of flexible but impervious material (such as 0.003 inch titanium metal, for example) is disposed in the cavity resting on gasket 14. A resilient O-ring 16 is disposed in the cavity on top of diaphragm 15 so as to engage the bottom chamfered edge of top member 11 so as to seal the unit when the top and bottom members are assembled and fastened together, as by means of a plurality of screws 17. Alternatively, the upper and lower body members and diaphragm may be welded together into an integral unit. A shallow recess in the bottom surface of the top member 11, along with the remaining space in the bottom body portion after assembly of the body, forms a shallow internal cavity which is divided by diaphragm 15 into a first or upper chamber 18 and a second or lower chamber 19.

The bottom body member 12 has an inlet passage 20 communicating with chamber 19 within the body, and an outlet passage 21 likewise communicating with that chamber. The outer ends of both passages are provided with fittings or adaptors 22 and 23, respectively. Fitting 22 is adapted to connect one end of a flow line 24 whose opposite end is connected to receive the discharge from a pressure actuated drug delivery system (FIG. 1), such as an implantable infusion pump, indicated generally at 25. Fitting 23 is adapted to connect to a catheter flow line 26 extending to the desired infusion site within the animal body. The interior end of outlet passage 21 terminates in a central recess 27 in the bottom wall of chamber 19. A resilient O-ring 28, whose thickness is greater than the depth of recess 27, is seated in the recess underlying diaphragm 15. The area between the top surface of O-ring 28 and diaphragm 15 forms a restricted flow passage when the diaphragm is flexed downwardly. If the pressure in chamber 18 is great enough, the diaphragm is forced into contact with O-ring 27 in order to shut off the flow through the outlet.

The upper body member 11 has an inlet passage 29 and outlet passage 30 extending into chamber 18 on the top side of diaphragm 15. The outer ends of passages 29 and 30 are provided with fittings 31 and 32, respectively. Fitting 31 is adapted to connect to a flow line connected to the discharge from a pressure actuated drug delivery device. such as implantable infusion pump 25. Fitting 32 is adapted to connect to the opposite end of flow line 24.

Flow line 24 includes one or more capillary restrictors 33, 33A upstream from inlet 20 and in series with the valve mechanism formed by diaphragm 15 and O-ring 28. In a preferred embodiment as illustrated, restrictors 33 and 33A are disposed in series in flow line 24. Restrictor 33A offers greater resistance to flow than does restrictor 33, ten times in one exemplary embodiment. A valved by-pass flow line 24A extends around restrictor 33A. The valve is ordinarily closed but may be opened (as described in my copending application Ser. No. 57,167, filed July 13, 1979) to permit the flow to by-pass restrictor 33A. This leaves restrictor 33 as the pressure drop element and permits increased flow of drug when needed, as in the case of increased flow of insulin to a diabetic patient for a period of time immediately following a meal. A variety of different flow rates may be selected through use of several restrictors of different resistances, along with corresponding valved bypass flow lines around the restrictors of greater resistance.

All parts of the flow regulator are formed from materials which are inert, non-toxic and bio-compatible, sterilizable and capable of long life in contact with the infusate and body fluids. Titanium is a preferred material for the body parts and fittings. The seals may be of any elastomer having the requisite properties, which also have good molding properties and long flex life. Surgical grade silicone rubber, polyurethane, and the like, are exemplary.

The exemplary drug delivery device, implantable infusion pump 25, comprises a housing 34 divided into a drug chamber 35 and a propellant chamber 36 by means of a bellows diaphragm 37. The infusion pump is implanted in an animal under the skin surface so that the drug chamber may be replenished hypodermically through the skin and through a penetrable resilient stopper 38. The propellant chamber contains a liquid whose vapor pressure is such that, under the conditions of normal body temperature, pressure is exerted upon the bellows to force the drug contained therein out through discharge opening 39 through the capillary flow line 40 to the flow regulator. If the pressure within the drug chamber 35 is $P_1$ and the pressure outside the drug delivery devide is $P_2$, then $\Delta P$, the pressure drop across capillary restrictor 33, is $P_1$ minus $P_2$.

Diaphragm 15 may be a flat disc supported between the top and bottom body members 11 and 12, as illustrated and described. Alternatively, the diaphragm may be supported by a bellows structure similar to that of bellows 37 of the infusion pump so as to extend either upwardly or downwardly. The diaphragm should be thin for easy flexing and smooth so as to engage the surface of O-ring 28 in sealing engagement. The pressure difference between chambers 18 and 19 is opposed by a spring which can be either the diaphragm's own resistance to deflection, or the resistance of a bellows, or a separate spring (not shown) pressing on the diaphragm.

Although reference is made herein to "top", "bottom", "upper", "lower", etc., these are relative only and are for purposes of ease in understanding the structure as illustrated. It is to be understood that when implanted in a body, the flow regulator may have whatever different orientation is appropriate under the existing circumstances. Although size is not a critical feature of the flow regulator, in one exemplary form diaphragm 15 is approximately 2.5 cm.

As best seen in FIG. 1, in the operation of the device the drug in chamber 35 is forced out through flow line 40 to flow regulator chamber 18, from that chamber to flow line 24 which includes capillary restrictor 33, into chamber 19 and out through flow line 26 to the desired infusion site.

Alternatively, although not preferred, chamber 18 may be dead-ended. That is, it has no outlet. Then, flow line 24 connects with flow line 40 so that the drug flow is directly to the restrictor 33 without passage through chamber 18, but that chamber is subject to the pressure of the drug supply chamber of pump 25.

Ordinarily the opposing forces on the diaphragm balance out and the diaphragm is stationary. If the forces are unbalanced, for example, by a decrease in flow that reduces the pressure difference across the capillary, the diaphragm will deflect. The diaphragm position determines the resistance to flow of the control valve. The control valve seal presses against the low pressure side of the diaphragm and, therefore, will open the valve when the pressure drop across the capillary is low and close the valve when the pressure drop is high. This negative feedback controls the flow to maintain it constant at a value determined by the balance of pressure on the diaphragm.

Flow rates as small as 1 ml/day may be controlled to within ±5 percent. This flow rate is so low that even small leakage paths through the valve would exceed the control range. The polished surface of the diaphragm forces the elastomer O-ring 28 to conform to its surface profile to reduce the leakage path to zero when fully seated. The diaphragm movement needed to go from fully seated to the flow rate of the desired dosage level is very small, which gives the valve a high effective gain as a control element.

Because the cavity containing chambers 18 and 19 is very shallow, only a small deflection of the diaphragm in either direction is permitted. This allows support for the diaphragm if over-pressured. It also permits a package envelope that is thin and can be easily placed within or attached to a delivery device such as the exemplary infusion pump. The flow control regulator makes possible the use of that pump as an insulin delivery system which requires close control. In the case of less critical drugs, such as heparin, the regulator is not necessary under ordinary conditions. However, its use does relieve the patient of the necessity to take special precautions during air travel or other situations when air pressure is reduced.

It is apparent that many modifications and variations of this invention as hereinbefore set forth may be made without departing from the spirit and scope thereof.

The specific embodiments described are given by way of example only and the invention is limited only by the terms of the appended claims.

The embodiments of the invention in which an exclusive property or privilege is claimed are defined as follows:

1. In a drug delivery system for implantation in an animal body for the infusion of liquid drugs into said body including a pressure actuated drug delivery device which is sensitive to ambient pressure and temperature conditions and a liquid catheter flow line for transfer of drug from the delivery device to an infusion site within the body, the improvement which consists in a pressure sensitive flow regulator in said flow line, said regulator comprising:
   (A) a body,
   (B) a shallow cavity within said body,
   (C) a flexible diaphragm in said body dividing said cavity into two chambers,
   (D) an inlet to the first of said chambers connected to the flow line,
   (E) an inlet to the second of said chambers connected to the flow line to receive the drug from the drug delivery device,
   (F) an outlet from the second of said chambers to the flow line downstream from the regulator, said outlet being centrally disposed in the wall of the cavity underlying said diaphragm, whereby flexing of the diaphragm in one direction in response to increased pressure in the flow line closes said outlet, and
   (G) at least one capillary flow restrictor in the flow line upstream from the inlet to the second chamber and in series with the inlet and outlet of said second chamber.

2. A flow regulator according to claim 1 wherein said outlet from said second chamber includes:
   (A) a shallow recess in the cavity wall, and
   (B) a resilient ring in said recess surrounding the outlet passage, the thickness of said ring being greater than the depth of said recess.

3. A flow regulator according to claim 1 wherein said body, diaphragm and fittings are composed of inert non-toxic biocompatible material.

4. A flow regulator according to claim 3 wherein said material is titanium.

5. A flow regulator according to claim 1 wherein:
   (A) an outlet is provided from said first chamber,
   (B) said outlet is provided with a fitting for connection to a capillary flow line extending to the inlet of said second chamber, whereby the flow from the drug delivery device to the infusion site is through the first chamber, and
   (C) said capillary restrictor is between said first chamber outlet and second chamber inlet.

6. A flow regulator according to claim 1 wherein:
   (A) said body is comprised of mating members, each having a cavity-forming recess in its inner face, and
   (B) said diaphragm is a thin disc supported at its periphery between said members.

7. A flow regulator according to claim 1 wherein:
   (A) said body is comprised of mating members, each having a cavity-forming recess in its inner face, and
   (B) said diaphragm is supported by a bellows.

8. A flow regulator according to claim 1 wherein:
   (A) at least two capillary restrictors of different flow resistance are upstream from the inlet to the second chamber and in series with the inlet and outlet of said second chamber, and
   (B) a valved by-pass flow line extends around the restrictor of greater resistance.

9. In a drug delivery system for implantation in an animal body for the infusion of liquid drugs into said body including a pressure actuated drug delivery device which is sensitive to ambient pressure and temperature conditions and a liquid catheter flow line for transfer of drug from the delivery device to an infusion site within the body, the improvement which consists in a pressure sensitive flow regulator in said flow line, said regulator comprising:
   (A) a body,
   (B) a shallow cavity within said body,
   (C) a flexible diaphragm in said body dividing said cavity into two chambers,
   (D) an inlet to the first of said chambers, said inlet being provided with a fitting for connection to the flow line from the drug delivery device,
   (E) an outlet from the first of said chambers,
   (F) an inlet to the second of said chambers,
   (G) a capillary flow line between said first chamber outlet and second chamber inlet, and
   (H) an outlet from the second of said chambers, said outlet including a centrally disposed shallow recess in the cavity wall and a resilient ring in said recess surrounding the outlet passage, the thickness of said ring being greater than the depth of said recess, whereby flexing of the diaphragm in one direction in response to increased pressure in the flow line closes the outlet, and a fitting for connection to the catheter flow line extending to an infusion site within the animal body, said regulator body, diaphragm and fittings being composed of inert, non-toxic biocompatible material.

10. A flow regulator according to claim 9 wherein said material is titanium.

11. A flow regulator according to claim 9 wherein:
   (A) at least two capillary flow restrictors of different flow resistance are upstream from the inlet to the second chamber and in series with the inlet and outlet of said second chamber, and
   (B) a valved by-pass flow line extends around the restrictor of greater resistance.

12. A system for implantation in an animal body for the infusion of liquid drugs into said body, said system comprising:
   (A) a pressure actuated drug delivery device comprising:
      (1) a housing,
      (2) a collapsible drug chamber within the housing,
      (3) an inlet passage to said drug chamber,
      (4) a penetrable resilient stopper in that passage,
      (5) a propellant chamber within the housing surrounding the drug chamber, and
      (6) a liquid within the propellant chamber whose vapor pressure is such that, under conditions of normal body temperature, pressure is exerted upon the collapsible chamber; and
   (B) a pressure sensitive flow regulator connected to the drug chamber of the drug delivery device and comprising:
      (1) a body,
      (2) a shallow cavity within said body,
      (3) a flexible diaphragm in said body dividing said cavity into two chambers,
      (4) an inlet to the first of said chambers, said inlet being connected to the drug chamber of the drug delivery device, (5) an inlet to the second of said chambers connected to receive the drug from the drug chamber, (6) an outlet from the second of said chambers, said outlet being centrally disposed in the wall of the cavity underlying said diaphragm, whereby flexing of the diaphragm in one direction closes said outlet, and (7) at least one flow restrictor in series with the inlet and outlet of said second chamber.

13. A system according to claim 12 wherein said outlet from said second chamber of the flow regulator includes:

(A) a shallow recess in the cavity wall, and (B) a resilient ring in said recess surrounding the outlet passage, the thickness of said ring being greater than the depth of said recess.

14. A system according to claim 12 wherein:

(A) said inlets to the flow regulator are provided with fittings for connection to a flow line from the drug delivery device, said flow line including at least one capillary restrictor, and (B) said outlet from the flow regulator is provided with a fitting for connection to a catheter flow line extending to an infusion site within the animal body.

15. A system according to claim 14 wherein:

(A) an outlet is provided from said first chamber of the flow regulator, (B) said outlet is provided with a fitting for connection to a capillary flow line extending to the inlet of said second chamber, whereby the flow from the drug delivery device to the infusion site is through the first chamber, and (C) said capillary restrictor is between said first chamber outlet and second chamber inlet.

16. A system according to claim 12 wherein:

(A) said body of the flow regulator is comprised of mating members, each having a cavity-forming recess in its inner face, and (B) said diaphragm is a thin disc supported at its periphery between said members.

17. A system according to claim 12 wherein:

(A) at least two capillary restrictors of different flow resistance are in series with the inlet and outlet of said second chamber of the flow regulator, and (B) a valve by-pass flow line extends around the restrictor of greater resistance.

* * * * *

UNITED STATES PATENT AND TRADEMARK OFFICE
CERTIFICATE OF CORRECTION

PATENT NO. : 4,299,220
DATED : November 10, 1981
INVENTOR(S) : Frank D. Dorman

It is certified that error appears in the above–identified patent and that said Letters Patent are hereby corrected as shown below:

Column 2, line 26, "light" should be --line--.

Column 3, line 61, "devide" should be --device--.

Signed and Sealed this

Twenty-third Day of November 1982

[SEAL]

Attest:

GERALD J. MOSSINGHOFF

Attesting Officer

Commissioner of Patents and Trademarks